United States Patent [19]

McDougald

[11] 4,075,323

[45] Feb. 21, 1978

[54] COCCIDIOCIDAL COMBINATIONS

[75] Inventor: Larry R. McDougald, Greenfield, Ind.

[73] Assignee: Eli Lilly and Company, Indianapolis, Ind.

[21] Appl. No.: 670,486

[22] Filed: Mar. 25, 1976

[51] Int. Cl.$^2$ ..................... A61K 35/66; A61K 31/35
[52] U.S. Cl. .................................... 424/114; 424/283
[58] Field of Search ................................ 424/283, 114

[56] References Cited

U.S. PATENT DOCUMENTS 3,501,568  3/1970  Haney et al. ......................... 424/283
3,719,753  3/1973  Berger et al. ........................ 424/283

*Primary Examiner*—Jerome D. Goldberg
*Attorney, Agent, or Firm*—William E. Maycock; Joseph A. Jones; Everet F. Smith

[57] ABSTRACT

Synergistic coccidiocidal combinations comprise two ionophorous fermentation-derived coccidiocides, each of which is administered to poultry in a concentration too low to produce satisfactory coccidiocidal effect alone. Preferred combinations include monensin and A204, monensin and lasalocid, and monensin and A28086.

2 Claims, No Drawings

COCCIDIOCIDAL COMBINATIONS

BACKGROUND OF THE INVENTION

This invention belongs to the field of poultry husbandry and provides new methods and compositions for the control of coccidiosis of poultry. The damage done by coccidiosis is well known. All of the economically reared poultry species are subject to infections of coccidia, which cause severe losses unless controlled. Coccidial infections not only cause the infected birds to gain weight more slowly than normal, and to convert their feed inefficiently, but often result in the deaths of large numbers of birds.

Like most parasitic infections, coccidiosis is most frequent and most damaging in flocks of birds reared in conditions of high population density. Since these conditions are also the most economical, modern efficient poultry operations are very likely to suffer severely from coccidiosis.

All of the coccidiocides used in this invention are known in the animal health art. References describing the compounds and their preparation will be cited below. The novelty of the present invention resides in the discovery that the compounds, when combined in proper amounts or concentrations, are synergistic. The coccidiocidal effect of the combinations is greater than the effect which could be expected from the known effects of the components of the combination, when used alone. Thus, use of the combinations allows the poultry grower to obtain economically satisfactory coccidiocidal effect with the administration of unusually small amounts of the coccidiocides. Small dosages not only have the obvious economic benefit, but also are likely to result in reduced residues of coccidiocide in the edible tissues of the poultry.

SUMMARY OF THE INVENTION

This invention provides a coccidiocidal composition for poultry comprising a coccidiocidally-ineffective concentration of each of two ionophorous fermentation-derived coccidiocides, which coccidiocides are synergistically coccidiocidally effective in combination, together with a poultry feedstuff or drinking water.

The preferred ionophorous fermentation-derived coccidiocides are as follows, together with the preferred concentrations in which they are to be used.

From about 20 to about 70 parts per million by weight (ppm) of monensin
From about 4 to about 20 ppm of A204
From about 80 to about 120 ppm of nigericin
From about 30 to about 50 ppm of A28086
From about 10 to about 20 ppm of A28695
From about 25 to about 50 ppm of lasalocid The terms monensin, A204, nigericin, A28086, A28695 and lasalocid are used herein to include the alkali metal, alkaline earth metal, ammonium and primary, secondary and tertiary $C_1$–$C_4$ alkylamine and $C_2$–$C_4$ hydroxyalkylamine salts thereof.

Preferred compositions include those wherein one of the coccidiocides is monensin, and its concentration is from about 20 to about 70 ppm.

Specific preferred compositions which are desirable embodiments of the invention include those wherein the following coccidiocides are used in the following concentrations in feed or drinking water:

From about 20 to about 70 ppm of monensin and from about 4 to about 20 ppm of A204.
From about 20 to about 70 ppm of monensin and from about 80 to about 120 ppm of nigericin.
From about 20 to about 70 ppm of monensin and from about 30 to about 50 ppm of A28086.
From about 20 to about 70 ppm of monensin and from about 10 to about 20 ppm of A28695.
From about 20 to about 70 ppm of monensin and from about 25 to about 50 ppm of lasalocid.
From about 30 to about 50 ppm of A28086 and from about 10 to about 20 ppm of A28695.
From about 4 to about 20 ppm of A204 and from about 10 to about 20 ppm of A28695.

Particularly preferred specific compositions include those wherein the following coccidiocides are used in the following concentrations:

From about 25 to about 50 ppm of monensin and from about 5 1 to about 16.5 ppm of A204.
From about 25 to about 50 ppm of monensin and about 100 ppm of nigericin.
From about 25 to about 50 ppm of monensin and from about 40 to about 45 ppm of A28086.
From about 25 to about 50 ppm of monensin and about 15 ppm of A28695.
From about 25 to about 50 ppm of monensin and about 37 ppm of lasalocid.
From about 40 to about 45 1 ppm of A28086 and about 15 ppm of A28695.
From about 5 to about 16.5 ppm of A204 and about 15 ppm of A28695.

This invention also provides a coccidiocidal method for poultry which comprises orally administering to the poultry a composition as described above.

DESCRIPTION OF THE PREFERRED EMBODIMENT

Most of the coccidiocides discussed here comprise two or more factors, like most products of fermentation origin. The various factors are all usable in this invention. As is usual in the art, the names of the coccidiocides are used herein to refer to the unresolved mixture of factors produced by fermentation, when a specific factor is not indicated.

The coccidiocides used in the present invention have been disclosed in the prior art. The compounds will be reviewed and references where their descriptions and preparations may be found will be named.

Monensin is described in U.S. Pat. No. 3,501,568, where it is called A3823 complex.

Another patent, U.S. Pat. No. 3,832,358, shows a modified form of monensin known as deshydroxymethylmonensin, which is likewise functional in the present invention.

A204 is disclosed by U.S. Pat. No. 3,705,238.

A28695 is described in U.S. Pat. No. 3,839,558.

Lasalocid, formerly known as X-537A, is discussed in U.S. Pat. No. 3,719,753. Lasalocid derivatives are disclosed and described in U.S. Pat. Nos. 3,873,715, 3,836,516, and 3,715,372. All of the derivatives of lasalocid, of course, may be used in this method equally as effectively as the parent compound.

Nigericin is described in U.S. Pat. No. 3,794,732.

A28086 is described in U.S. Patent Applications No. 569,740 and 569,719, both filed Apr. 21, 1975. The disclosures of both applications are herein incorporated by reference.

The following matter describes A28086 and the microorganisms and fermentation processes which produce it.

Antibiotic A-28086 factor A crystallizes from acetone-water, and melts at about 98°–100° C., resolidifies and remelts at about 195°–200° C. Elemental analysis of factor A gave the following average percentage composition: carbon, 66.69 percent; hydrogen, 9.85 percent; oxygen, 23.10 percent. The empirical formula proposed for factor A is $C_{43}H_{72}O_{11}$.

Factor A has an apparent molecular weight of 764 as determined by mass spectrometry.

The infrared spectrum of factor A in chloroform showed the following absorption maxima: 2.85, 3.34, 5.83, 6.82, 7.22, 7.53 (weak), 7.78 (weak), 8.75 (strong), 8.95 (strong), 9.15, 9.50 (strong), 9.55 (strong), 9.60, 9.85, 10.15, 10.45, and 10.70 (weak) microns.

The ultraviolet spectrum of factor A in ethanol shows only end absorption below 220 m$\mu$.

The nuclear magnetic resonance spectrum of A-28086 factor A in deuterochloroform showed the following characteristics: $\delta$ 6.01, 4.21, 4.11, 3.99, 3.89, 3.80, 3.67, 3.65, 3.57, 3.55, 2.83, 2.76, 2.74, 2.68, 2.66, 2.58, 2.56, 2.30, 2.22, 2.17, 2.10, 2.05, 1.96, 1.90, 1.85, 1.70, 1.62, 1.60, 1.47, 1.39, 1.31, 1.25, 1.18, 0.95, 0.93, 0.90, 0.88, 0.85, 0.77, 0.75, 0.73, 0.68, and 0.66 ppm.

Antibiotic A-28086 factor A, crystallized from acetone-water, has the following characteristic X-ray powder diffraction pattern ($Cu^{++}$ radiation, 1.5405$\lambda$, nickel filter, $d$ = interplanar spacing in angstroms):

| d | Relative Intensity |
|---|---|
| 12.00 | 100 |
| 10.10 | 50 |
| 9.25 | 90 |
| 8.00 | 40 |
| 7.50 | 15 |
| 6.92 | 90 |
| 6.40 | 40 |
| 5.98 | 05 |
| 5.68 | 15 |
| 5.20 | 40 |
| 4.98 | 40 |
| 4.62 | 40 |
| 4.21 | 20 |
| 3.48 | 10 |

The specific rotation of antibiotic A-28086 factor A is −54° ($c=0.2$, methanol), when determined at a temperature of 25° C. This specific rotation is an average value, based on several determinations.

Electrometric titration of factor A in 80% aqueous dimethylformamide indicated the presence of a titratable group with a $pK_a$ value of 7.9.

Antibiotic A-28086 factor A is soluble in a variety of organic solvents such as methanol, ethanol, dimethylformamide, dimethyl sulfoxide, ethyl acetate, chloroform, acetone, and benzene; but is only slightly soluble in non-polar organic solvents such as hexane; and is insoluble in water.

Antibiotic A-28086 factor B is a white crystalline compound (from acetone-water) which has a melting point of about 150°–153° C.

As determined by high-resolution mass spectrometry, factor B has an apparent molecular weight of 762 and a proposed empirical formula of $C_{43}H_{70}O_{11}$.

The infrared spectrum of factor B in chloroform showed the following absorption maxima: 2.82, 3.30, 5.77, 5.85, 6.80, 7.20, 7.50 (weak), 7.72 (weak), 7.80 (weak), 8.57 (strong), 8.68, 8.90 (strong), 9.10, 9.50, 9.83 (strong), 9.90, 10.10, 10.17 (strong), 10.43 (weak), 10.80 (weak), 11.20 (weak), 11.35 (weak), 11.73 (weak), and 12.03 (weak) microns.

The ultraviolet spectrum of factor B in ethanol shows an absorption maximum at 220 m$\mu$ ($E_{1cm}^{1\%}$ 32 137.5; $\epsilon = 10,477$).

The nuclear magnetic resonance spectrum of A-28086 factor B in deuterochloroform showed the following characteristics: $\delta$ 7.20, 7.09, 6.26, 6.15, 4.19, 4.12, 4.05, 3.95, 3.89, 3.78, 3.62, 3.59, 3.52, 3.48, 2.81, 2.73, 2.63, 2.54, 2.52, 1.99, 1.91, 1.84, 1.71, 1.67, 1.64, 1.55, 1.43, 1.33, 1.18, 1.11, 0.96, 0.94, 0.90, 0.87, 0.84, 0.77, 0.74, and 0.68 ppm.

Antibiotic A-28086 factor B is soluble in a variety of organic solvents such as, for example, methanol, ethanol, dimethylformamide, dimethyl sulfoxide, ethyl acetate, chloroform, acetone and benzene; but is only slightly soluble in nonpolar organic solvents such as hexane; and is insoluble in water.

Although the chemical structure of A-28086 antibiotic factor B has not been elucidated, the physical-chemical data thus far available indicate that factor B has a single carboxylic acid moiety, two ketone moieties, and one or more hydroxyl moieties.

Antibiotic A-28086 factor D is a white crystalline material (from water-acetone) with a melting point of about 96°–98° C. A-28086 factor D has an apparent molecular weight of 778, as determined by high-resolution mass spectrometry.

The elemental composition of the peak in the mass spectrum of the sodium salt of A-28086 factor D was observed to be 800.5050 (Calcd for $C_{44}H_{73}O_{11}Na$ = 800.5050). In the mass spectrum of A-28086 factor D free acid, a small peak at 778 and a larger peak at 760.5117 (Calcd for $C_{44}H_{72}O_{10}$ = 760.5125) were observed. The m/e 760 in the mass spectrum of the free acid results from the loss of water from the molecular ion. The molecular-ion composition of A-28086 factor D free acid is, therefore, $C_{44}H_{74}O_{11}$.

The empirical formula proposed for A-28086 factor D is $C_{44}H_{74}O_{11}$. Elemental analysis of factor D gave the following percentage composition: carbon, 67.59 percent; hydrogen 9.38 percent; oxygen, 22.77 percent.

The theoretical percentage composition for $C_{44}H_{74}O_{11}$ is: carbon, 67.87 percent; hydrogen, 9.51 percent; oxygen, 22.77 percent.

The infrared absorption spectrum of A-28086 factor D contains the following observable absorption maxima: 2.89, 3.39, 3.43, 3.50, 5.88, 6.90, 7.27, 7.60, 7.84, 9.00, 9.26, 9.62, 10.31, 10.58, 11.10, and 11.49 microns.

A-28086 factor D in 95 percent aqueous ethanol shows no ultraviolet absorption.

The nuclear magnetic resonance spectrum of A-28086 factor D in deuterochloroform showed the following characteristics: $\delta$ 6.00, 4.20, 4.10, 4.00, 3.98, 3.92, 3.86, 3.83, 3.79, 3.67, 3.64, 3.57, 3.54, 2.88, 2.81, 2.71, 2.62, 2.58, 2.48, 2.43, 2.37, 2.29, 2.21, 2.15, 2.10, 2.04, 1.97, 1.89, 1.83, 1.76, 1.68, 1.61, 1.58, 1.55, 1.47, 1.39, 1.30, 1.25, 1.18, 0.95, 0.90, 0.88, 0.84, 0.74, and 0.68 ppm.

Antibiotic A-28086 factor D, crystallized from acetone-water, has the following characteristic X-ray powder-diffraction pattern ($Cu_{++}$ radiation, 1.5405$\lambda$, nickel filter, $d$ = interplanar spacing in angstroms):

| d | Relative Intensity |
|---|---|
| 12.40 | 100 |
| 10.20 | 70 |
| 8.85 | 90 |
| 7.80 | 30 |
| 6.80 | 10 |
| 6.30 | 100 |

-continued

| d | Relative Intensity |
|---|---|
| 5.70 | 20 |
| 5.35 | 20 |
| 5.10 | 20 |
| 4.90 | 10 |
| 4.65 | 20 |
| 4.45 | 40 |
| 4.20 | 30 |
| 3.30 | 10 |
| 3.15 | 10 |
| 2.99 | 05 |
| 2.77 | 05 |
| 2.28 | 05 |

The specific rotation of antibiotic A-28086 factor D is $-56°$ (c = 0.1, methanol), when determined at a temperature of 25° C.

Electrometric titration of A-28086 factor D in 80 percent aqueous dimethylformamide indicated the presence of a titratable group with a $pK_a$ value of 8.67.

Antibiotic A-28086 factor D is soluble in a variety of organic solvents such as methanol, ethanol, dimethylformamide, dimethyl sulfoxide, ethyl acetate, chloroform, acetone and benzene. A-28086 factor D is only slightly soluble in nonpolar organic solvents such as hexane and is insoluble in water.

Antibiotic A-28086 factor D has an acid function capable of forming salts and ester derivatives and at least one hydroxyl group capable of esterification.

The $R_f$ values of antibiotic A-28086 factors A, B and D in various paper-chromatographic systems, using Bacillus subtilis ATCC 6633 as a detection organism, are given in Table I.

TABLE I

| $R_f$ Value | | | |
|---|---|---|---|
| Factor A | Factor B | Factor D | Solvent System |
| 0.11 | 0.09 | 0.10 | Water saturated with methyl isobutyl ketone (MIBK) |
| 0.41 | 0.16 | 0.26 | Water saturated with MIBK plus 2% p-toluenesulfonic acid and 1% piperidine |
| 0.54 | 0.46 | 0.36 | Water:methanol:acetone (12:3:1)- adjusted to pH 10.5 with NH$_4$OH and then lowered to pH 7.5 with H$_3$PO$_4$ |
| 0.48 | 0.36 | 0.29 | 1% MIBK, 0.5% NH$_4$OH in water |
| 0.15 | 0.33 | 0.25 | 17.4 g K$_2$HPO$_4$, 30 ml ethanol per liter of water |
| 0.24 | 0.51 | 0.26 | Benzene saturated with water |
| 0.24 | 0.11 | 0.09 | Water |
| 0.75 | 0.61 | 0.64 | Water:MIBK:ethyl acetate (98:1:1) |

In Table II are given the $R_f$ values for antibiotic A-28086 factors A, B and D in two thin-layer-chromatographic systems on silica gel (precoated plates, E. Merck, Darmstadt, F-254, layer thickness 0.25 mm), again using B. subtilis ATCC 6633 as a detection organism.

TABLE II

| $R_f$ Values | | | |
|---|---|---|---|
| Factor A | Factor B | Factor D | Solvent System |
| 0.24 | 0.42 | 0.26 | Benzene-ethyl acetate (3:2) |
| 0.54 | 0.34 | 0.66 | Ethyl acetate-diethylamine (95:5) |

Another substance, arbitrarily designated as A-28086-I, is co-produced with the antibiotic A-28086 complex. Although A-28086-I is not microbiologically active, it is structurally related to the A-28086 antibiotic factors. A-28086-I is a white crystalline compound (from acetone-water) and has a melting point of about 160°–162° C. Comparative studies of the NMR spectra and other properties of A-28086-I and synthetically-prepared A-28086 factor A methyl ester give evidence that A-28086-I is the methyl ester, formed on the acid group, of A-28086 factor A or a closely related compound such as a stereoisomer.

Although A-28086-I initially co-precipitates with the active A-28086 antibiotic factors, it is readily separated from them by silica gel chromatography. A-28086-I has an approximate $R_f$ value of 0.53 on silica gel thin-layer chromatography with ethyl acetate as the eluting solvent and using vanillin spray reagent (3% vanillin in methanol + 0.5 ml conc H$_2$SO$_4$ per 100 ml of solution) for detection. After spraying with vanillin and heating, A-28086-I gives a blue spot while the A-28086 antibiotic factors give bright pink spots which quickly turn dark brownish-blue.

The compounds are produced by culturing an A-28086-producing strain of Steptomyces aureofaciens, either NRRL 5758 or NRRL 8092, under submerged aerobic conditions in a suitable culture medium until substantial antibiotic activity is produced. The antibiotics are recovered by employing various isolation and purification procedures commonly used and understood in the art.

The organisms are classified as strains of S. aureofaciens Duggar, as described by E. B. Shirling and D. Gottlieb in "Cooperative Description of Type Cultures of Streptomyces. III. Additional Species Descriptions from First and Second Studies," Intern. Bull. Systematic Bacteriol. 18, 279–392 (1968).

CHARACTERIZATION OF A-28086-PRODUCING STRAIN NRRL 5758

Morphology

Sporulating aerial hyphae consist of hooks, loops and open spirals. Also observed was morphology representative of the rectus flexibilis type. Spores are short and cylindrical and are in chains of 10–50 spores. The spores measure 1.3μ × 1.75μ with a range of 1.3μ to 1.95 × 1.3μ.

The spore surface, as observed by electron microscopy, is smooth.

| Cultural Characteristics of NRRL 5758 on Various Media | |
|---|---|
| Medium | Characteristics |
| ISP No. 2 (yeast extract-malt extract) | Growth-abundant; reverse moderate yellow [11K3]; fair-to-good aerial mycelium and sporulation; white (W) 13 ba and dark gray (Gy) 3 ih; no soluble pigment. |
| ISP No. 3 (oatmeal) | Growth-good; reverse grayish yellow [11B2]; fair aerial mycelium (Gy) dark gray, 3 ih; slight brown soluble pigment. |
| ISP No. 4 (inorganic salts-starch agar) | Growth-abundant; reverse light yellow brown [12E5]; aerial mycelium and spore (W) purplish white 13 ba to (Gy) light gray d; no soluble pigment. |
| ISP No. 5 (glycerol-asparagine agar) | Growth-good; reverse pale yellow-green [10B1]; good aerial mycelium and spores |

| Cultural Characteristics of NRRL 5758 on Various Media | |
| --- | --- |
| Medium | Characteristics |
| | (Gy) yellowish gray 2 dc, to light grayish reddish brown 5 fe; no soluble pigment. |
| Tomato paste-oatmeal agar | Growth-abundant; reverse light yellow brown [13H7]; fair to good aerial mycelium and spores (W) white a to (Gy) medium gray g; very slight brown soluble pigment. |
| Glycerol-glycine agar | Growth-abundant; reverse dark grayish yellow [12I6]; good aerial mycelium and spores (Y) pale yellow 2 db; no soluble pigment. |
| Glucose-asparagine agar | Growth-abundant; reverse grayish greenish yellow [12E2]; abundant aerial mycelium and spores (Gy) yellowish gray 2 dc; very slight brown soluble pigment. |
| Nutrient agar | Growth-good; reverse grayish yellow [12B2]; aerial myceliuman spores, no color assignment because of poor growth; no soluble pigment. |
| Bennett's agar | Growth-abundant, reverse grayish yellow [12K3]; scant aerial mycelium and spores (Gy) yellowish gray 2 dc; no soluble pigment. |
| Calcium malate agar | Growth-good; reverse grayish brown [15C8]; no aerial mycelium or sporulation; brown soluble pigment. Area by inoculum cleared. |
| Czapek's solution agar | Growth-poor; no color assignment due to poor growth. |
| Emerson's agar | Growth-abundant; reverse grayish yellow [11J5]; no aerial mycelium or spores; no soluble pigment. |
| Tyrosine agar | Growth-abundant; reverse light olive brown [14C4]; abundant aerial mycelium and spores from (W) b (center) to (Gy) light brownish gray 3 fe (margin); very slight brown soluble pigment. |
| Tryptone-yeast agar | Growth-scant; no-color assignment. |

The NRRL 5758 organism was studied for selected physiological properties in accordance with standard procedures. The properties observed and characteristics found were as follows:

| Property Observed | Characteristic |
| --- | --- |
| Action on milk | Milk peptonized, white growth ring; cleared area tannish yellow-pH reaction 5.7 |
| Nitrate reduction | Positive |
| Nutrient gelatin | 30% liquefaction at 14 days |
| Melanin pigment production on: | |
| Tyrosine-agar slants | Very weak positive (pigment after 4 days) |
| Difco peptone yeast extract | Negative |
| Iron agar slants Tryptone-yeast-extract broth | Negative |
| Temperature requirements (ISP medium No. 2 yeast extract malt extract slants) | 26–30° C-good growth; 30–37° C.-excellent growth and sporulation; 45° C.-slight vegetative growth; reddish soluble pigment. |

The results of carbon utilization tests carried out with organism NRRL 5758 are set forth below. The symbols used to indicate growth response are:

```
+    good growth, positive utilization
(+)  poor to fair growth
(−)  faint growth, probably no utilization
−    no growth, no utilization
```

| Carbon Source | Response |
| --- | --- |
| D-glucose | + |
| L-arabinose | + |
| D-xylose | + |
| D-fructose | + |
| sucrose | − |
| D-mannitol | − |
| i-inositol | + |
| rhamnose | + |
| raffinose | − |
| -C control (no carbohydrate) | − |

A second new A-28086-producing organism was derived from S. aureofaciens NRRL 5758 by a series of natural selections, followed by chemical mutation, and is identified as NRRL 8092.

CHARACTERIZATION OF A-28086-PRODUCING STRAIN NRRL 8092

Morphology

On medium ISP No. 7 (tyrosine agar) the culture produces occasional hooks, but mainly produces short, straight sporophores. Spore chains are less than 10 spores per chain, usually 4–7 spores per chain. Short straight spore chains were observed in the following media: ISP No. 3, Czapek's-solution agar and ISP No. 5. Abundant coremia were observed on Emerson's agar. Electron microscope observations were made on tyrosine agar (ISP No. 7) and glucose-asparagine agar. Spores are smooth and range in size from 1.2 to 2.0$\mu$ in length and about 1.0$\mu$ in diameter. The average spore size is 1.6$\mu$ × 1.0$\mu$.

| Cultural Characteristics of NRRL 8092 on Various Media | |
| --- | --- |
| Medium | Characteristics |
| ISP No. 2 (yeast extract-malt extract) | Growth-fair; reverse light yellow brown [12H8]; fair aerial mycelium; poor sporulation; aerial pale gray [11A1]; no soluble pigment. |
| ISP No. 3 (oatmeal) | Growth-sparse; reverse hyaline; no aerial mycelium; no soluble pigment. |
| ISP No. 4 (inorganic salts-starch agar) | Growth-moderate; reverse grayish yellow [11B2]; scant aerial mycelium and sporulation; aerial pale yellow gray [10A1]; no soluble pigment. |
| ISP No. 5 (glycerol-asparagine agar) | Growth-moderate; reverse pale yellow [10F2]; fair aerial mycelium; scant sporulation; aerial white [10A1]; no soluble pigment. |
| Tomato paste-oatmeal agar | Growth moderate; reverse grayish green-yellow; aerial mycelium fair; moderate sporulaton, light pale gray [53A2]; no soluble pigment. |
| Glycerol-glycine agar | Growth-abundant; reverse grayish yellow [11E4]; moderate aerial mycelium, white [10A1]; no sporulation; no soluble pigment. |
| Glucose-asparagine agar | Growth-moderate; reverse pale yellow ( 10F2]; moderate aerial mycelium and sporulation, white [10A1]; no soluble pigment. |

| Cultural Characteristics of NRRL 8092 on Various Media | |
|---|---|
| Medium | Characteristics |
| Nutrient agar | Growth-sparse; reverse pale yellow [10B2]; no aerial mycelium; no soluble pigment. |
| Bennett's agar | Growth-fair; reverse medium yellow pink [11A7]; very scant aerial mycelium; no sporulation; no soluble pigment. |
| Calcium malate agar | Growth-very scant, hyaline; no aerial mycelium; no soluble pigment. |
| Czapek's solution agar | Growth-very scant; reverse hyaline; no aerial mycelium; no soluble pigment. |
| Emerson's agar | Growth-moderate; reverse grayish yellow [11I5]; spotty aerial mycelium; no sporulation; no soluble pigment. |
| Tyrosine agar | Growth-moderate; reverse light yellow brown [12H6]; moderate aerial mycelium, light pale gray margin [53A2], center near white, and moderate sporulation; no soluble pigment. |
| Tryptone-yeast agar | Growth-very scant, hyaline; no aerial mycelium; no soluble pigment. |

Organism NRRL 8092 was also studied for selected physiological properties in accordance with standard procedures. The properties observed and characteristics found were as follows:

| Property Observed | Characteristic |
|---|---|
| Action on milk | Peptonized (90%); pale-yellow growth ring, cleared area pale yellow--pH reaction 4.6 |
| Nitrate reduction | Positive |
| Nutrient gelatin | 50% hydrolyzed at 14 days |
| Melanin pigment production on: | |
| Tyrosine-agar slants | Very weakly positive |
| Tryptone-yeast-extract broth | Negative |
| Carrot plug | Abundant growth, pale yellow; no aerial mycelium |
| Potato plug | Abundant growth, grayish white; no aerial mycelium; no change in plug. |
| Temperature requirements (ISP medium No. 2 yeast extract malt extract slants) | 25° C.-Abundant growth; fair aerial mycelium; reverse light brown; no soluble pigment. 30° C.-Abundant growth; fair aerial mycelium; reverse light brown; no soluble pigment. 37° C.-Abundant growth; fair aerial mycelium; reverse-brown; soluble pigment brown. 40° C.-Abundant growth; sparse aerial mycelium; reverse red brown; soluble pigment deep red brown. 45° C.-Fair growth; no aerial mycelium; reverse red brown; moderate red brown pigment. |

The results of carbon utilization tests carried out with organism NRRL 8092 are set forth below.

| Carbon Source | Response |
|---|---|
| D-glucose | + |
| L-arabinose | + |
| D-xylose | + |
| D-fructose | + |
| sucrose | − |
| D-mannitol | − |
| i-inositol | + |
| rhamnose | + |
| raffinose | − |
| -C control (no carbohydrate) | − |

Certain characteristics of the A-28086-producing S. aureofaciens strains differ from the characteristics of the organism described by Shirling and Gottlieb. These differences are summarized in Table III:

TABLE III

| Carbon utilization | NRRL 5758 | NRRL 8092 | Published Description |
|---|---|---|---|
| sucrose | − | − | + |
| i-inositol | + | + | − |
| rhamnose | + | + | − |
| Gelatin Liquefaction | 30% in 14 days | 50% in 14 days | Limited or None |
| Action on Milk | Milk peptonized, white growth ring | Milk peptonized, pale-yellow growth ring | Limited and variable peptonization (often none); limited growth and coagulation |

The characteristics of organism NRRL 5758 which differ from the characteristics of organism NRRL 8092 are summarized in Table IV.

TABLE IV

| Characteristic | NRRL 5758 | NRRL 8092 |
|---|---|---|
| Vegatative Color | Yellow on several media | Cream to pale-yellow on several media |
| Sporulaton | Some spiral sporophores on tomato-paste:oatmeal and inorganic salts-starch media | Short straight sporophores with occasional hooks |
| Growth on: | | |
| Calcium malate | Growth fair, brown; with clearing | Growth sparse, clear, no clearing |
| Inorganic salts-starch | Moderate sporulation; aerial purplish white to gray. | Scant sporulation aerial pale yellow gray |
| Bennett's agar | Reverse pale-yellow | Reverse pink |

The S. aureofaciens cultures useful for production of A-28086 antibiotics have been deposited and made a part of the stock culture collection of the Northern Marketing and Nurition Research Division, U.S. Dept. of Agriculture, Agricultural Research Service, Peoria, Ill., 61604, from which they are available to the public under the numbers NRRL 5758 and NRRL 8092.

The culture medium employed to grow S. aureofaciens NRRL 5758 or S. aureofaciens NRRL 8092 can be any one of a number of media. For economy in production, optimal yield, and ease of product isolation, however, certain culture media are preferred. Thus, for example, preferred carbohydrate sources in large-scale fermentation are tapioca dextrin and sucrose, although glucose, corn starch, fructose, mannose, maltose, lactose, and the like can also be employed. Corn oil, peanut oil, soybean oil and fish oil are other useful sources of carbon. A preferred nitrogen source is enzyme-hydrolyzed casein, although peptones, soybean meal, cottonseed meal, amino acids such as glutamic acid, and the like are also useful. Among the nutrient inorganic salts which can be incorporated in the culture media are the customary soluble salts capable of yielding sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e. 0.2 ml/l.) of an antifoam agent such as polypropylene glycol to large-scale fermentation media if foaming becomes a problem.

For production of substantial quantities of the A-28086 antibiotics, submerged aerobic fermentation in tanks is preferred. Small quantities of the A-28086 antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that employed for larger fermentations, but other media can also be employed.

The A-28086-producing organisms can be grown at temperatures between about 20° and about 40° C. Optimum A-28086 production appears to occur at temperatures of about 27°–30° C.

As is customary in aerobic submerged culture processes, sterile air is blown through the culture medium. For efficient growth of the organism the volume of air employed in the tank production is preferably above 0.1 volume of air per volume of culture medium per minute. For efficient production of the A-28086 antibiotics the volume of air employed in the tank production is preferably above 0.25 volume of air per volume of culture medium per minute. High levels of dissolved oxygen do not depress antibiotic production.

The initial pH of the uninoculated culture medium varies with the medium used. In general, the pH should be in the range of 6.0 to 7.5. The harvest pH at the end of the fermentation is usually slightly higher, in the range of 6.5 to 8.0.

Generally, antibiotic activity is detectable on the second day of the fermentation. Maximum production of antibiotic activity usually occurs between about the sixth and the tenth days.

Following their production under submerged aerobic fermentation conditions, the A-28086 antibiotics previously described can be recovered from the fermentation medium by methods commonly employed in the fermentation art. The antibiotic activity produced during fermentation of an A28086-producing organism occurs in both the mycelial mass and in the filtered broth. Maximum recovery of the A-28086 antibiotics is accomplished, therefore, by a combination of methods, including filtration, extraction, and adsorption chromatography. A preferred solvent for separating the A-28086 antibiotics from either whole or filtered fermentation broth is ethyl acetate, although other commonly used solvents are satisfactory.

An especially advantageous method of separating the A-28086 factors A, B and D is to lower the pH of the whole fermentation broth to about pH 3.0. At this pH the A-28086 factors A, B, and D are conveniently separated with the mycelial mass by filtration. Another advantageous method of separating the A-28086 factors involves adding a bicarbonate such as, for example, sodium bicarbonate, to the whole broth in amounts of approximately one gram per liter. The A-28086 factors are, thereby, conveniently separated with the mycelial mass in salt form. Methanol is a preferred solvent for separating the antibiotics from the mycelial mass, but other lower alcohols and ketones are also suitable.

Azeotropic distillation can also be advantageously employed in the recovery of the A-28086 antibiotics. In this method an organic solvent which forms an appropriate azeotrope with water is added to the aqueous fermentation broth. This solvent-broth mixture is subjected to azeotropic distillation in order to remove at least half the water from the broth, leaving a water-solvent mixture in which the A-28086 antibiotics are in solution in the organic solvent. Insoluble by-products can be separated by suitable means such as filtration or centrifugation. The A-28086 antibiotics can then be recovered from the organic solution by well-known procedures such as evaporation of solvent, precipitation by adding a nonsolvent, or extraction.

Further purification of the A-28086 antibiotics includes additional extraction and adsorption procedures. Adsorptive materials such as silica gel, carbon, Florisil ® (magnesium silicate, Floridin Co., P.O. Box 989, Tallahassee, Fla.) and the like can be advantageously employed.

Alternatively, the culture solids, including medium constituents and mycelium can be used without extraction or separation, but preferably after removal of water, as a source of the A-28086 antibiotics. For example, after production of A-28086 antibiotic activity, the culture medium can be dried by lyophilization and mixed directly into feed premix.

In another aspect, after production of A-28086 activity in the culture medium, the mycelium can be separated and dried to give a product which can be used directly in a feed premix.

Under the conditions employed thus far, the *S. aureofaciens* strains described previously and designated as NRRL 5758 and NRRL 8092 produce antibiotic A-28086 factor A as the predominant factor. Although the ratio of factors varies depending on the fermentation conditions used, in general factor A accounts for more than 99 percent of the total recovered antibiotic activity from NRRL 5758 and for about 90 percent of the total recovered antibiotic activity from NRRL 8092. A-28086 factor B accounts for most of the remianing antibiotic activity from NRRL 5758, and factor D is a minor factor. On the other hand, A-28086 factor D accounts for about 8–10 percent of the total recovered antibiotic activity from NRRL 8092, and factor B is a minor factor.

Antibiotic A-28086 factors A, B, and D are separated from each other and are isolated as individual compounds by the use of well-known methods such as column chromotography, thin-layer chromatography and the like. For example, column chromatography over silica gel is used to separate factors A, B, and D by eluting the column with varying solvent mixtures, such as benzene-ethyl acetate. Using benzene-ethyl acetate solvent mixtures over a silica gel column, factor B is eluted first, and factors A and D are eluted later. Thin-layer chromatography, as described hereinabove, is a convenient method for monitoring elution progress.

EXAMPLE 1

A. Shake-flask Fermentation of A-28086 using *S. aureofaciens* NRRL 5758

A culture of *S. aureofaciens* NRRL 5758 was prepared and maintained in an agar slant having the following composition:

| Ingredient | Amount |
| --- | --- |
| Agar | 20 g |
| Dextrin | 10 g |
| Enzyme-hydrolyzed casein | 2 g |
| Beef extract | 2 g |
| Yeast extract | 2 g |
| Distilled water | q.s. 1 liter |

The slant was inoculated with *S. aureofaciens* NRRL 5758, and the inoculated slant was incubated at 30° C. for 6 to 10 days. The mature slant culture was covered with beef serum, and scraped with a sterile loop to loosen the spores. The resulting beef-serum suspension of spores and mycelial fragments was lyophilized into six pellets.

One lyophilized pellet thus prepared was used to inoculate 50 ml of a vegetative medium having the following composition:

| Ingredient | Amount |
| --- | --- |
| Glucose | 20 g |
| Soybean grits | 15 g |
| Corn-steep liquor | 10 g |
| CaCO$_3$ | 2 g |
| Tap Water | q.s. 1 liter |

The inoculated vegetative medium, in a 250-ml Erlenmeyer flask, was incubated at 30° C. for 72 hours on a shaker rotating through an arc 2 inches in diameter at 250 rpm.

B. Tank Fermentation of A-28086 using *S. aureofaciens* NRRL 5758

In order to provide a larger volume of inoculum, 10 ml of the incubated vegetative medium described above was used to inoculate 400 ml of a second-stage vegetative growth medium having the same composition as that of the vegetative medium. This second-stage medium, in a 2-liter flask, was incubated at 30° C. for 24 hours on a shaker rotating through an arc 2 inches in diameter at 250 rpm.

This second-stage vegetative medium (1 liter) was used to inoculated 100 liters of sterile production medium of the following composition:

| Ingredient | Amount |
| --- | --- |
| Tapioca dextrin | 60.0 g/l |
| Enzyme-hydrolyzed casein | 8.0 g/l |
| Molasses | 15.0 g/l |
| MgSO$_4$ . 7H$_2$O | 0.5 g/l |
| CaCO$_3$ | 2.0 g/l |
| Refined soybean oil | 5.0 g/l |
| Deionized water | q.s. 1 liter |

The pH of the medium was 6.7 after sterilization by autoclaving at 120° C. for 30 minutes at 15–20 pounds pressure. In a 165-liter fermentation tank, the inoculated production medium was allowed to ferment for 10 days at a temperature of 29° C. The fermentation medium was aerated with sterile air at the rate of 0.4 volume of air per volume of culture medium per minute. The medium was stirred with conventional agitators at 250 rpm.

EXAMPLE 2

The A-28086 antibiotics were produced according to the process of Example 1, but utilizing a flask-production medium having the following composition:

| Ingredient | Amount |
| --- | --- |
| Glucose | 10 g/l |
| Edible molasses | 20 g/l |
| Peptone | 5 g/l |
| CaCO$_3$ | 2 g/l |
| Tap Water | q.s. 1 liter |

Separation of the A-28086 Antibiotic Complex Produced by *S. aureofaciens* NRRL 5758

Whole fermentation broth (132 liters), obtained by the method described in Example 1, as filtered with a filter aid (Hyflo Super-cel, a diatomaceous earth, Johns-Manville Products Corp.) to give 97 liters of filtered broth. The filered broth was extracted with an approximately equal volume of ethyl acetate. The ethyl acetate extract was separated from the aqueous phase and was concentrated to a volume of about 500 ml. This concentrated ethyl acetate extract was added to a large excess of petroleum ether (Skellysolve F; about 10 liters) to precipitate and, thereby, separate unwanted material. The separated filtrate was evaporated under vacuum to give the broth portion of A-28086 antibiotic complex (6.9 g).

The mycelial portion of A-28086 antibiotic complex was obtained by extracting the filtered mycelium twice with approximately half volumes of methanol (62 liters and 59 liters). The two methanol extracts were combined and were concentrated under vacuum to remove the methanol. After this concentration about 10 liters of an aqueous phase remained. This aqueous phase was adjusted to about pH 7.5 with dilute sodium hydroxide. The resulting solution was extracted twice with approximately equal volumes of ethyl acetate (9 liters and 10 liters). The ethyl acetate extracts were combined and then concentrated to a volume of about 400 ml. This concentrated ethyl acetate extract was added to a large excess of petroleum ether to remove unwanted materials, using the procedure described above for the concentrated filtered broth extract. The mycelial portion of A-28086 antibiotic complex obtained from the filtrate weighed 20.6 g.

EXAMPLE 4

Isolation of A-28086 Individual Factors A and B

The mycelial portion of A-28086 antibiotic complex (235 g, prepared as described in Example 3) was dissolved in about 80 ml of benzene. This benzene solution was applied to a silica gel column (9 × 130 cm, 8 liters, Matheson grade 62 silica gel). The column was eluted with varying benzene-ethyl acetate mixtures. Elution progress was followed by thin-layer chromatography. Using a benzene-ethyl acetate (90:10) solvent system, factor B was eluted first and was isolated as an individual factor. Factor B (43 mg) was crystallized from acetone-water, m.p. 150°–153° C.

Continuing to elute with benzene-ethyl acetate mixtures but gradually increasing the ratio of ethyl acetate present, factor A was eluted; the various fractions containing factor A were combined and were concentrated under vacuum to a residue. This residue was dissolved in acetone (about 150 ml); water (about 150 ml) was added to the acetone solution. The pH of the resulting solution was adjusted to pH 3 by the addition of 1N hydrochloric acid. The acidified mixture was stirred about one hour, during which time a precipitate formed. This precipitate was separated by filtration and was recrystallized from acetone (about 150 ml) upon addition of water (about 60 ml). The product was dried overnight under vacuum to give factor A (about 6.6 g). After partial evaporation of acetone from the filtrate, a second crop of factor A (about 1.2 g) was obtained.

EXAMPLE 5

A-28086 Factor A-Acetyl Ester Derivative

Antibiotic A-28086 factor A (7.4 g) was dissolved in pyridine (150 ml). Acetic anhydride (50 ml) was added to this solution. The resulting solution was mixed thoroughly and then was allowed to stand overnight at room temperature.

Water (200 ml) was added, mixing thoroughly. This mixture was allowed to stand for 4 hours at room temperature. A white solid precipitated; this solid was separated by filtration, washed with water, and air dried. The resulting solid was dissolved in acetone (100 ml); and the acetone solution was evaporated to dryness under vacuum (this was repeated three times). The residue thus obtained crystallized from acetone (100 ml)-water (50 ml), to give A-28086 factor A acetyl derivative (6.14 g), melting point 100°–103° C.

EXAMPLES 6–9

Antibiotic A-28086 factor A propionyl ester derivative, prepared by reacting factor A with propionic anhydride in the presence of pyridine according to the method of Example 5, melting point 96°–98° C.

Antibiotic A-28086 factor A n-butyryl ester derivative, prepared by reacting factor A with n-butyric anhydride in the presence of pyridine according to the method of Example 5, melting point 79°–81° C.

Antibiotic A-28086 factor A n-caproyl ester derivative, prepared by reacting factor A with caproic anhydride in the presence of pyridine according to the method of Example 5, melting point 163°–167° C.

Antibiotic A-28086 factor A n-valeryl ester derivative, prepared by reacting factor A with valeric anhydride in the presence of pyridine according to the method of Example 5, melting point 173°–175° C.

EXAMPLE 10

Preparation of A-28086 Factor A Sodium Salt

Antibiotic A-28086 factor A (500 mg) was dissolved in acetone (50 ml). Water (50 ml) was added to this solution, and 5N sodium hydroxide was added to bring the pH of the solution to 10.5-11. The resulting solution was stirred for 1 hour and then extracted with ethyl acetate. The ethyl acetate extract was evaporated to dryness under vacuum. The residue was precipitated from an acetone-water solution to give 378 mg of A-28086 factor A sodium salt, melting point 120°–123° C.

EXAMPLES 11–15

Antibiotic A-28086 factor A barium salt was prepared from antibiotic A-28086 factor A (500 mg) and saturated barium hydroxide, using the method of Example 10 to give 369 mg of A-28086 factor A barium salt, melting point 188°–190° C.

Antibiotic A-28086 factor A potassium salt was prepared from antibiotic A-28086 factor A (500 mg) and 5N potassium hydroxide, using the method of Example 10 to give 363 mg of A-28086 factor A potassium salt, melting point 165°–167° C.

Antibiotic A-28086 factor A cesium salt was prepared from antibiotic A-28086 factor A (500 mg) and 1N cesium hydroxide, using the method of Example 10 to give 540 mg of A-28086 factor A cesium salt, melting point 190°–210° C.

Antibiotic A-28086 factor B sodium salt, prepared from antibiotic A-28086 factor B and 5N sodium hydroxide according to the method of Example 10.

EXAMPLE 16

Shake-flask Fermentation of A-28086 using S. aureofaciens NRRL 8092

A culture of S. aureofaciens NRRL 8092 was prepared and maintained on an agar slant having the following composition:

| Ingredient | Amount |
| --- | --- |
| $K_2HPO_4$ | 2 g |
| $MgSO_4 \cdot 7H_2O$ | 0.25 g |
| $NH_4NO_3$ | 2 g |
| $CaCO_3$ | 2.5 g |
| $FeSO_4 \cdot 7H_2O$ | 0.001 g |
| $MnCl_2 \cdot 7H_2O$ | 0.001 g |
| $ZnSO_4 \cdot 7H_2O$ | 0.001 g |
| Glucose | 10 g |
| Agar | 20 g |
| Deionized water | q.s. 1 liter |
| pH (unadjusted) | 7.7 |

The slant was inoculated with S. aureofaciens NRRL 8092, and the inoculated slant was incubated at 30° C for about 7 days. The mature slant culture was covered with sterile beef serum and was scraped with a sterile loop to prepare a spore and mycelial suspension from the slant culture. The resulting suspension was lyophilized into a maximum of six pellets.

One of the lyophile pellets thus prepared was used to inoculate 50 ml of a vegetative medium having the following composition:

| Ingredient | Amount |
| --- | --- |
| Glucose | 20 g |
| Soybean flour | 15 g |
| Corn-steep liquor | 10 g |
| $CaCO_3$ | 2 g |
| Tap Water | q.s. 1 liter |
| pH adjusted to pH 6.5 with dil NaOH | |

The inoculated vegetative medium, in a 250-ml Erlenmeyer flask, was incubated at 30° C. for 48 hours on a rotary shaker at 250 rpm with a 2-inch arc.

The incubated vegetative medium described above (0.5 ml, 1 percent) was used to inoculate 50 ml of a fermentation medium having the following composition:

| Ingredient | Amount |
| --- | --- |
| Tapioca dextrin* | 60.0 g |
| Enzyme-hydrolyzed casein** | 6.0 g |
| Enzymatic hydrolysate of casein*** | 2.0 g |
| CaCO₃ | 2.0 g |
| MgSO₄ . 7H₂O | 0.5 g |
| Blackstrap molasses | 15.0 g |
| Refined soybean oil | 5.0 ml |
| Tap Water | q.s. 1 liter |
| pH (unadjusted) 6.6 | |

*Staley Dextrin No. 11, A. E. Staley Co., Decatur, Ill.
**Amber EHC, Amber Laboratories, Juneau, Wisc.
***NZ Amine A, Sheffield Chemical Co., Norwich, N.Y.

EXAMPLE 17

Tank Fermentation of A-28086 using *S. aureofaciens* NRRL 8092

The initial procedure described in Example 16 for the shake-flask fermentation of A-28086 was also used for tank fermentation. In order to produce a larger volume of inoculum, 10 ml of the incubated vegetative medium was used to inoculate 400 ml of a second-stage vegetative medium having the same composition as that of the first vegetative medium. This second-stage medium, in a 2-liter Erlenmeyer flask, was incubated at 30° C. for 24 hours on a rotary shaker at 250 rpm with a 2-inch arc.

This incubated second-stage vegetative medium (800 ml) was used to inoculate 100 liters of sterile fermentation medium having the following composition:

| Ingredient | Amount |
| --- | --- |
| Tapioca dextrin* | 60.0 g/l |
| Enzyme-hydrolyzed casein** | 6.0 g/l |
| Enzymatic-hydrolysate of casein*** | 2.0 g/l |
| CaCO₃ | 2.0 g/l |
| MgSO₄ . 7H₂O | 0.5 g/l |
| Blackstrap molasses | 15.0 g/l |
| Refined soybean oil | 5.0 mg/l |
| Tap Water | q.s. 1 liter |

*Staley Dextrin No. 11, A. E. Staley Co., Decatur, Ill.
**Amber EHC, Amber Laboratories, Juneau, Wisc.
***NZ Amine A, Sheffield Chemical Co., Norwich, N.Y.

The pH of the medium was 6.8 ± 0.1 after sterilization by autoclaving at 121° C. for 30 minutes at 15-20 pounds pressure. In a 165-liter fermentation tank, the inoculated production medium was allowed to ferment for 10-12 days at 28 ± 1° C. The fermentation medium was aerated with sterile air at the rate of 0.4 volume of air per volume of culture medium per minute. The medium was stirred with conventional agitators at 300 rpm.

EXAMPLE 18

Separation of the A-28086 Antibiotic Complex Produced by *S. aureofaciens* NRRL 8092

Whole fermentation broth (60 liters), obtained by the method described in Example 17, was adjusted to pH 3 by the addition of dilute HCl. The resulting solution was filtered using a filter aid (Hyflo Super-cel, a diatomaceous earth, Johns-Manville Products Corp.). The separated mycelial cake was extracted with 30 liters of methanol, adding 1.56 kg of NaHCO₃ to the extract with stirring. After separation of this extract, the mycelial cake was again extracted with another 30 liters of methanol. The two methanol extracts were combined and concentrated under vacuum to remove the methanol. The remaining aqueous solution (about 7 liters) was adjusted to pH 7.5 with dilute HCl. The resulting solution was extracted twice with ethyl acetate (7-liter portions). The ethyl acetate extracts were combined and concentrated under vacuum to given an oily residue. This oily residue was dissolved in 1500 ml of acetone. Water (1500 ml) was added to the acetone solution. The resulting solution was adjusted to pH 3 with dilute HCl and was stirred one hour. The precipitate which had formed was separated by filtration and then was dissolved in acetone (1500 ml); water (400 ml) was added to this solution. The resulting solution was allowed to stand for 16 hours for crystallization to occur. The crystals formed were separated by filtration and dried under vacuum to give 74 g crude crystalline product containing A-28086 factors A, B and D and crystalline impurities.

This crude crystalline product (40 g) was dissolved in about 250 ml of benzene. The benzene solution was then applied to a silica-gel column (9- × 120-cm column; Grace-Davidson grade 62 silica gel). The column was eluted successively with 40 liters of each of the following:
(1) benzene
(2) benzene:ethyl acetate (9:1)
(3) benzene:ethyl acetate (4:1)
(4) benzene:ethyl acetate (7:3)
(5) benzene:ethyl acetate (1:1)
(6) ethyl acetate
(7) methanol One-liter fractions were collected. Each fraction was checked by assay against *Bacillus subtilis* and by thin-layer chromatography to identify the eluted compounds. A-28086I was eluted with benzene:ethyl acetate (4:1). A-28086 factor B was eluted with benzene:ethyl acetate (7:3). A-28086 factors A and D were eluted in the fractions obtained with benzene:ethyl acetate (7:3 and 1:1), fractions 119–156. These fractions were combined and evaporated to dryness under vacuum. The residue thus obtained was dissolved in acetone (500 ml). Water (500 ml) was added to the acetone solution, and the resulting solution was adjusted to pH 3 with dilute HCl and was stirred for one hour. The precipitate which formed was separated by filtration and was crystallized from acetone (500 ml)-water (180 ml). The crystals thus formed were separated by filtration and dried under vacuum to give 20.1 g of a mixture of A-28086 factors A and D.

EXAMPLE 19

Separation and Purification of Individual Factors A and D

The crystalline mixture of A-28086 factors A and D obtained in Example 18 (18.8 g) was dissolved in benzene (50 ml). The benzene solution was applied to a silica-gel column (7- × 100-cm column; E. Merck grade 60 silica gel, finer than 230 mesh ASTM). The column was eluted, at a flow rate of 90 ml per hour, successively with:
(1) 12 liters of benzene
(2) 12 liters of benzene:ethyl acetate (9:1)
(3) 12 liters of benzene:ethyl acetate (4:1)
(4) 32 liters of benzene:ethyl acetate (7:3)
(5) 10 liters of methanol One-to two-liter fractions were collected until activity was detected; then 200-ml fractions were collected. The fractions containing only A-28086 factor D were combined and evaporated under vacuum to a residue.

This residue crystallized from acetone-water (1:1). The crystals were separated and dried under vacuum to give 140 mg of crystalline A-28086 factor D.

The fractions containing A-28086 factor D with a trace of A-28086 factor A were treated in the same manner to give an additional 150 mg of crystalline A-28086 factor D containing a small amount of A-28086 factor A.

The fractions containing only A-28086 factor A were also treated in the same manner to give 4.7 g of crystalline A-28086 factor A.

EXAMPLE 20

Preparation of A-28086 Factor D Sodium Salt

Antibiotic A-28086 factor D is dissolved in acetone. An equivalent amount of water is added to this solution, and sufficient 5N sodium hydroxide is added to bring the pH of the solution to about pH 11. The resulting solution is stirred for about an hour and then is extracted with ethyl acetate. The ethyl acetate extract is evaporated under vacuum to give A-28086 factor D sodium salt.

EXAMPLES 21-23

Antibiotic A-28086 factor D potassium salt, prepared from A-28086 factor D and 5N potassium hydroxide, using the method of Example 10.

Antibiotic A-28086 factor D barium salt, prepared from A-28086 factor D and saturated barium hydroxide, using the method of Example 10.

Antibiotic A-28086 factor D cesium salt, prepared from A-28086 factor D and 1N cesium hydroxide, using the method of Example 10.

Further ionophorous coccidiocides exemplary of those which may be used in the practice of this invention include A150, U.S. Pat. No. 3,711,605; salinomycin, U.S. Pat. No. 3,857,948; dianemycin, U.S. Pat. No. 3,577,531; and X206, U.S. Pat. No. 3,794,732.

The ionophorous coccidiocides used in this invention have hydroxyl groups, which may be esterified to form acyl esters. Such esters, particularly the $C_2$-$C_6$ alkanoyl esters, are equivalent to the coccidiocides and may be used in the practice of the present invention. Esterification occurs at one or more of the hydroxyl groups upon simple treatment with a $C_2$-$C_6$ carboxylic acid anhydride or acid halide, for example, at room temperature in methanol.

The compounds used in this invention, and the acyl esters thereof, form physiologically-acceptable salts. Accordingly, the physiologically-acceptable alkali metal, alkaline earth metal and amine salts of the compounds and of their $C_2$-$C_6$ alkanoyl ester derivatives are also used in this invention. "Physiologically-acceptable" salts are salts in which the toxicity of the compound as a whole toward warm-blooded animals is not increased relative to the non-salt form. Representative alkali-metal and alkaline-earth-metal salts include the sodium, potassium, lithium, cesium, rubidium, barium, calcium and magnesium salts.

Suitable amine salts include the ammonium and the primary, secondary and tertiary $C_1$-$C_4$ alkylamine and $C_2$-$C_4$ hydroxyalkylamine salts. Illustrative amine salts include those formed by reaction of the coccidiocides with ammonium hydroxide, methylamine, s-butylamine, isopropylamine, diethylamine, diisopropylamine, ethanolamine, triethylamine, 3-amino-1-propanol and the like.

The salts of the coccidiocides are prepared according to the general procedures commonly employed for the preparation of cationic salts. For example, the free acid form of the compound is dissolved in a suitable solvent, and an aqueous or organic solvent solution of the desired base is added to the coccidiocide solution. The salts are isolated by filtration or by evaporation of the solvent.

It is well known in the veterinary pharmaceutical art that conditions within the treated animal or bird frequently change a compound to chemical forms other than that in which it was administered. Therefore, the form in which it may be administered does not affect the method of treatment and may be chosen for reasons of economics or convenience. All of the compounds described herein, therefore, may be administered in the form of any desired alkanoyl ester or salt without effect on the efficacy of the invention.

The following exemplary coccidiocides are typical of the alkanoyl ester and salt forms in which the compounds of this invention may be used. The compounds are mentioned only to assure that the reader fully understands the invention, and are not to be interpreted as bounding the scope of the usable compounds.

monensin diacetate
nigericin propionate, lithium salt
A204 acetate, magnesium salt
A28086, sodium salt
A28695 butyrate
lasalocid acetate, ammonium salt
A204 pentanoate
monensin, potassium salt
A204 acetate, ethylamine salt
nigericin, ethanolamine salt
A28086 hexanoate
A28695, triethylamine salt
monensin propionate, s-butylamine salt
A28695 acetate
monensin, diethylamine salt
A204 pentanoate, potassium salt
nigericin, calcium salt
A28695, barium salt
lasalocid propionate, methylamine salt
lasalocid, ammonium salt
monensin, isopropanolamine salt
nigericin, dimethylamine salt
A28695, magnesium salt
A28695 hexanoate
A28086 propionate
A28086, calcium salt The present invention has been tested by in vivo experiments with chickens infected with coccidiosis. The following tests are exemplary of the efficacy of various embodiments of the invention.

In the tests described below, the coccidiocides were used as the unresolved mixtures of factors produced by fermentation. All of the compounds, except A28086, were in the form of sodium or mixed sodium-potassium salts. A28086 was used as the free acid.

Untreated, infected control birds and untreated normal control birds were used in all experiments described below. The birds used were from a homogeneous research flock, and the *E. tenella* culture used to infect the birds was from a laboratory strain known to reproduce consistently and to produce uniform infections. Each bird was orally inoculated with 20,000–40,000 sporulated oocysts. The coccidiocides were mixed with the birds' feed in concentrations, measured in ppm., shown in the tables below.

The extent of coccidial infection is expressed as a lesion score on an arbitrary 0–4 scale. At the end of the tests, all birds were killed, and their intestinal tracts were examined. Birds which showed none of the lesions left by coccidia were scored 0, and birds with extremely severe infections were scored 4. Intermediate degrees of infection were given lesion scores of 1, 2 or 3. The scores of all the birds which received a given treatment were averaged.

TEST 1 monensin + A204

One-week-old broiler cockerels were allotted to 10-bird cages and were fed medicated or control ration for one day prior to infection with *E. tenella*. The birds were maintained on the same rations for seven days and infections were scored as described above. Each cage constituted a treatment group.

| Treatment | Concentration | Lesion Score |
| --- | --- | --- |
| None | 0 | 3.9 |
| monensin | 50 | 2.1 |
| A204 | 5.5 | 3.3 |
| A204 | 16.5 | 0.6 |
| monensin + A204 | 50 + 5.5 | 1.4 |
| monensin + A204 | 50 + 16.5 | 0 |

TEST 2 monensin + A204

This test was conducted in the same fashion as the test above, eacept that each treatment group comprised five birds.

| Treatment | Concentration | Lesion Score |
| --- | --- | --- |
| None | 0 | 3.0 |
| monensin | 50 | 2.4 |
| A204 | 5.5 | 3.0 |
| A204 | 7.7 | 2.6 |
| A204 | 12.1 | 1.6 |
| A204 | 16.5 | 0.2 |
| monensin + A204 | 50 + 5.5 | 0.4 |
| monensin + A204 | 50 + 7.7 | 0.4 |
| monensin + A204 | 50 + 12.1 | 0.4 |
| monensin + A204 | 50 + 16.5 | 0 |

TEST 3 monensin + A204

The procedure in this test followed the procedure of Test 1.

| Treatment | Concentration | Lesion Score |
| --- | --- | --- |
| None | 0 | 3.3 |
| monensin | 25 | 3.4 |
| monensin | 50 | 2.5 |
| A204 | 5 | 3.1 |
| A204 | 10 | 1.6 |
| monensin + A204 | 25 + 5 | 2.7 |
| monensin + A204 | 25 + 10 | 1.2 |
| monensin + A204 | 50 + 5 | 1.9 |
| monensin + A204 | 50 + 10 | 0.9 |

TEST 4 monensin + A204

This test followed the procedure of Test 1, except that each treatment group consisted of three cages of 10 birds each.

| Treatment | Concentration | Lesion Score |
| --- | --- | --- |
| None | 0 | 2.9 |
| monensin | 50 | 1.7 |
| A204 | 5.5 | 2.3 |
| monensin + A204 | 50 + 5.5 | 0.6 |

TEST 5 monensin + A204

The procedure of this test followed that of Test 1 again, except that each treatment group comprised 5 replicates of 5 birds per cage.

| Treatment | Concentration | Lesion Score |
| --- | --- | --- |
| None | 0 | 3.0 |
| monensin | 50 | 2.2 |
| A204 | 7 | 2.2 |
| monensin + A204 | 50 + 7 | 0.9 |

TEST 6 monensin + nigericin

In this test, the procedure of Test 1 was used.

| Treatment | Concentration | Lesion Score |
| --- | --- | --- |
| None | 0 | 3.4 |
| monensin | 50 | 2.2 |
| nigericin | 100 | 2.8 |
| monensin + nigericin | 50 + 100 | 0.4 |

TEST 7 monensin + nigericin

The procedure of Test 5 was used.

| Treatment | Concentration | Lesion Score |
| --- | --- | --- |
| None | 0 | 3.0 |
| monensin | 50 | 2.2 |
| nigericin | 100 | 2.4 |
| monensin + nigericin | 50 + 100 | 0.5 |

TEST 8 monensin + A28086

The procedure of Test 1 was used.

| Treatment | Concentration | Lesion Score |
| --- | --- | --- |
| None | 0 | 3.4 |
| monensin | 50 | 2.2 |
| A28086 | 42 | 2.8 |
| monensin + A28086 | 50 + 42 | 1.4 |

TEST 9 monensin + A28086
The procedure of Test 1 was used.

| Treatment | Concentration | Lesion Score |
|---|---|---|
| None | 0 | 3.3 |
| monensin | 25 | 3.4 |
| monensin | 50 | 2.5 |
| A28086 | 40 | 2.4 |
| monensin + A28086 | 25 + 40 | 1.3 |
| monensin + A28086 | 50 + 40 | 1.0 |

TEST 10 monensin + A28086
The procedure of Test 5 was used.

| Treatment | Concentration | Lesion Score |
|---|---|---|
| None | 0 | 3.0 |
| monensin | 50 | 2.2 |
| A28086 | 45 | 2.5 |
| monensin + A28086 | 50 + 45 | 0.6 |

TEST 11 monensin + A28695
The procedure of Test 1 was used.

| Treatment | Concentration | Lesion Score |
|---|---|---|
| None | 0 | 3.4 |
| monensin | 50 | 2.2 |
| A28695 | 15 | 3.2 |
| monensin + A28695 | 50 + 15 | 0.4 |

TEST 12 monensin + A28695
The procedure of Test 1 was used, except that each treatment group consisted of three cages of 10 birds each.

| Treatment | Concentration | Lesion Score |
|---|---|---|
| None | 0 | 2.7 |
| monensin | 50 | 1.7 |
| A28695 | 15 | 2.5 |
| monensin + A28695 | 50 + 15 | 0.6 |

TEST 13 monensin + A28695
The procedure of Test 5 was used.

| Treatment | Concentration | Lesion Score |
|---|---|---|
| None | 0 | 3.0 |
| monensin | 50 | 2.2 |
| A28695 | 15 | 2.6 |
| monensin + A28695 | 50 + 15 | 0.8 |

TEST 14 monensin + lasalocid
The procedure of Test 1 was followed, except that the chicks were orally infected with 60,000 E. tenella oocysts per bird. Each treatment group comprised five replicates of five birds each.

| Treatment | Concentration | Lesion Score |
|---|---|---|
| None | 0 | 3.5 |
| monensin | 50 | 3.2 |
| lasalocid | 37 | 3.3 |
| monensin + lasalocid | 50 + 37 | 0.6 |

TEST 15

A28086 + A28695
The procedure of Test 1 was followed.

| Treatment | Concentration | Lesion Score |
|---|---|---|
| None | 0 | 3.4 |
| A28086 | 42 | 2.8 |
| A28695 | 15 | 3.2 |
| A28086 + A28695 | 42 + 15 | 1.7 |

TEST 16

A204 + A28695
The procedure of Test 5 was followed.

| Treatment | Concentration | Lesion Score |
|---|---|---|
| None | 0 | 3.0 |
| A204 | 7 | 2.2 |
| A28695 | 15 | 2.6 |
| A204 + A28695 | 7 + 15 | 0.7 |

The present invention is useful to protect poultry in general. Not only such barnyard fowl as chickens, turkeys, ducks and geese may be protected thereby, but also exotic fowl such as pheasants and quail.

Coccidiosis is likely to affect poultry of any age and in any type of cultural practice. The present invention, therefore, may be used at any time to protect poultry from coccidiosis. As noted above, however, coccidiosis is most likely to affect poultry being reared in confined quarters, as in broiler houses and the like. Use of the invention in poultry reared under such conditions, therefore, will provide particularly great benefits.

Since coccidiosis is likely to break out at any time, use of this invention is recommended at any time of year and may be continued for any length of time. Continuous administration of a composition of this invention throughout the lives of the poultry is a particularly useful embodiment of the invention. However, the administration of a composition of this invention for even short periods of time, such as a few days, will also produce benefits and is a useful manner in which to carry out the method of this invention.

The compositions and methods of this invention are used for the control of coccidiosis in the usual fashion. Coccidiosis of poultry directly affects the intestinal tract, and anticoccidial drugs are therefore administered orally. The compositions of this invention, accordingly, are compositions wherein the synergistic coccidiocides are combined with either a poultry feedstuff or with drinking water. The compositions are novel only because of the presence therein of the synergistic coccidiocides, and otherwise follow conventional practices in the feedstuff industry.

The concentrations of the coccidiocides which are named herein are based on food or drinking water compositions which are the entire food or drinking water supply of the poultry. This method of describing the concentrations of the coccidiocides is in accordance with the practice of the poultry industry, since it is normal to supply to poultry only one source of food and one source of drinking water. Those of skill in poultry husbandry will recognize, however, that the concentrations must be adjusted upward, should it be desirable to supply the poultry with various sources of food or water, only part of which are compositions of this invention.

Poultry feedstuffs made according to all formulae and manners used in the poultry industry are perfectly satisfactory as carriers for the synergistic coccidiocides of this invention. The following poultry feedstuff formulae are representative of formulae typically used in the industry and are listed to assist the reader. A poultry scientist or grower will understand from inspection of the following formulae, however, that the formulation of the poultry feedstuff is not a limiting factor in the use of this invention. Feedstuffs based on any grain and containing any vitamin concentrate, mineral concentrate or other drugs and feed additives are satisfactory. Both conventional dry and pelleted feeds and liquid suspension feeds including feeds based on distiller's wastes and milk byproducts may be used in the compositions of this invention.

| Turkey Starter | |
|---|---|
| Ingredients | Percent |
| soybean meal, solvent extracted, dehulled | 40.7 |
| corn, yellow, ground | 39.7 |
| fish meal with solubles | 5.0 |
| beef tallow | 5.0 |
| corn distillers dried solubles | 2.5 |
| alfalfa meal, dehydrated (17%) | 2.5 |
| dicalcium phosphate feed grade | 2.5 |
| calcium carbonate | 1.2 |
| vitamin premix[1] | 0.5 |
| salt (NaCl) | 0.2 |
| trace mineral premix[2] | 0.1 |
| methionine hydroxy analog | 0.1 |
| Total | 100.0 |

| Turkey Finisher | |
|---|---|
| Ingredients | Percent |
| corn, yellow, ground | 71.2 |
| soybean meal, solvent extracted, dehulled (50%) | 9.9 |
| corn distillers dried solubles | 5.0 |
| alfalfa meal, dehydrated (17%) | 5.0 |
| animal fat | 3.0 |
| fish meal with solubles | 2.5 |
| dicalcium phosphate, feed grade | 1.7 |
| calcium carbonate | 0.5 |
| vitamin premix[1] | 0.5 |
| salt (NaCl) | 0.4 |
| methionine hydroxy analog | 0.2 |
| trace mineral premix[2] | 0.1 |
| Total | 100.0 |

| Chick Starter, Light Breeds | |
|---|---|
| Ingredients | Percent |
| corn, yellow, ground | 56.3 |
| soybean meal, solvent extracted, dehulled (50%) | 17.9 |
| wheat middlings | 10.0 |
| corn distillers dried solubles | 5.0 |
| fish meal with solubles | 5.0 |
| alfalfa meal, dehydrated (17%) | 2.5 |
| dicalcium phosphate, feed grade | 1.3 |
| calcium carbonate | 0.9 |
| vitamin premix[1] | 0.5 |
| salt (NaCl) | 0.3 |
| methionine hydroxy analog | 0.2 |
| trace mineral premix[2] | 0.1 |
| Total | 100.0 |

| Pullet Grower | |
|---|---|
| Ingredients | Percent |
| corn, yellow, ground | 73.5 |
| soybean meal, solvent extracted, dehulled (50%) | 21.9 |
| dicalcium phosphate, feed grade | 2.5 |
| calcium carbonate | 1.0 |
| vitamin premix[1] | 0.5 |
| salt (NaCl) | 0.3 |
| methionine hydroxy analog | 0.2 |
| trace mineral premix[2] | 0.1 |
| Total | 100.0 |

| Pullet Developer | |
|---|---|
| Ingredients | Percent |
| corn, yellow, ground | 67.5 |
| oats, ground whole | 15.0 |
| soybean meal, solvent extracted, dehulled (50%) | 13.4 |
| dicalcium phosphate, feed grade | 2.1 |
| calcium carbonate | 1.0 |
| vitamin premix[1] | 0.5 |
| methionine hydroxy analog | 0.3 |
| salt (NaCl) | 0.2 |
| trace mineral premix[2] | 0.1 |
| Total | 100.0 |

| Layer, Light Breeds | |
|---|---|
| Ingredients | Percent |
| corn, yellow, ground | 61.00 |
| calcium carbonate | 8.50 |
| soybean meal, solvent extracted, dehulled (50%) | 8.25 |
| oats, ground whole | 5.00 |
| wheat middlings | 5.00 |
| corn distillers dried solubles | 5.00 |
| alfalfa meal, dehydrated (17%) | 2.50 |
| fish meal with solubles | 2.00 |
| dicalcium phosphate, feed grade | 1.60 |
| vitamin premix[1] | 0.50 |
| salt (NaCl) | 0.30 |
| methionine hydroxy analog | 0.25 |
| trace mineral premix[2] | 0.10 |
| Total | 100.00 |

| Pullet Grower, Broiler Breeders | |
|---|---|
| Ingredients | Percent |
| corn, yellow, ground | 38.1 |
| oats, ground whole | 30.0 |
| soybean meal, solvent extracted, dehulled (50%) | 12.8 |
| wheat middlings | 10.0 |
| alfalfa meal, dehydrated (17%) | 5.0 |
| dicalcium phosphate, feed grade | 1.7 |
| calcium carbonate | 1.3 |
| vitamin premix[1] | 0.5 |
| methionine hydroxy analog | 0.3 |
| salt (NaCl) | 0.2 |
| trace mineral premix[2] | 0.1 |
| Total | 100.0 |

| Pullet Developer, Broiler Breeders | |
|---|---|
| Ingredients | Percent |
| corn, yellow, ground | 54.5 |
| oats, ground whole | 15.0 |
| wheat middlings | 10.0 |
| alfalfa meal, dehydrated (17%) | 7.5 |
| corn distillers dried solubles | 5.0 |
| fish meal with solubles | 2.5 |
| soybean meal, solvent extracted, dehulled (50%) | 1.9 |
| dicalcium phosphate, feed grade | 1.4 |
| calcium carbonate | 1.1 |
| vitamin premix[1] | 0.5 |
| salt (NaCl) | 0.3 |
| methionine hydroxy analog | 0.2 |
| trace mineral premix[2] | 0.1 |
| Total | 100.0 |

| Broiler Breeder | |
|---|---|
| Ingredients | Percent |
| corn, yellow, ground | 42.8 |
| oats, ground whole | 25.0 |
| soybean meal, solvent extracted, dehulled (50%) | 8.1 |

| | |
|---|---|
| wheat middlings | 5.0 |
| corn distillers dried solubles | 5.0 |
| fish meal with solubles | 2.5 |
| alfalfa meal, dehydrated (17%) | 2.5 |
| calcium carbonate | 6.3 |
| dicalcium phosphate, feed grade | 1.7 |
| vitamin premix[1] | 0.5 |
| salt (NaCl) | 0.3 |
| methionine hydroxy analog | 0.2 |
| trace mineral premix[2] | 0.1 |
| Total | 100.0 |

[1] vitamin premix provides 3000 IU of Vitamin A, 900 ICU of Vitamin D, 40 mg of Vitamin E, 0.7 mg of Vitamin K, 1000 mg of choline, 70 mg of niacin, 4 mg of pantothenic acid, 4 mg of riboflavin, 0.10 mg of Vitamin $B_{12}$, 0.10 mg of biotin and 125 mg of ethoxyquin per kg of complete feed.

[2] trace mineral premix provides 75 mg of manganese, 50 mg of zinc, 25 mg of iron and 1 mg of iodine per kg of complete feed.

It will be understood that poultry feed compositions according to this invention will usually be made by first preparing a concentrated premix which contains the synergistic coccidiocides in high concentrations, such as from about 0.25 percent to about 80 percent by weight. Such premixes comprise the coccidiocides dispersed in such physiologically-acceptable carriers as polyethylene glycols, propylene glycol, inert oils including vegetable oils and highly-refined mineral oils, ethanol, water, aqueous alcohols, vermiculite, diatomaceous earth, attapulgite, cracked corn, soybean meal, alfalfa meal, rice hulls, ground corncob, and the like.

The synergistic coccidiocides of this invention are also readily administered in the drinking water of poultry. They are incorporated into drinking water by merely adding a water-soluble or water-suspendible form of the compounds to water in the proper amount. Such compositions are most easily prepared by choosing a water-soluble form of the compounds. If an insoluble form is preferred, however, a suspension may be made. Suspensions are prepared by proper use of physiologically-acceptable adjuvants to keep the compounds in suspension in the water. Adjuvants are chosen from among the thickeners, such as carboxymethylcellulose, polyvinylpyrrolidone, gelatin and the alginates. Many classes of surfactants also serve to suspend the compounds. For example, lecithin, alkylphenol polyethylene oxide adducts, naphthalene sulfonates, alkylbenzene sulfonates, and the polyoxyethylene sorbitan esters are useful for preparing suspensions. It is usually most practical to prepare a concentrated suspension, or a dry formulation of the synergistic coccidiocides and suspending agents, which concentrated formulation is diluted in plain drinking water for administration to poultry.

It will be understood by both chemists and poultry scientists that the method of this invention may be combined with other methods of treating and nourishing poultry. For example, a composition according to the present invention may be further fortified or medicated with growth promoting agents, antibiotic drugs, parasiticides and the like without impairing the efficacy of the present invention.

While the primary thrust of this invention is the protection of poultry from coccidiosis, it will be apparent that other animals may be protected thereby, as well.

I claim:

1. A coccidiocidal composition for poultry comprising a coccidiocidally-ineffective concentration of each of two ionophorous fermentation-derived coccidiocides, which coccidiocides are synergistically coccidiocidally effective in combination, together with a poultry feedstuff or drinking water, wherein the coccidiocides and the concentrations thereof are about 50 ppm of monensin and about 37 ppm of lasalocid.

2. A coccidiocidal method for poultry which comprises orally administering to the poultry a coccidiocidally-effective combination of about 50 ppm of monensin and about 37 ppm of lasalocid, together with a poultry feedstuff or drinking water.

* * * * *

UNITED STATES PATENT OFFICE
CERTIFICATE OF CORRECTION

Patent No. 4,075,323           Dated February 21, 1978

Inventor(s) Larry R. McDougald

It is certified that error appears in the above-identified patent and that said Letters Patent are hereby corrected as shown below:

Column 2, line 17: "5 1 to" should read --5 to--.

Column 2, line 26: "45 1 ppm" should read --45 ppm--.

Column 4, line 2: "$E_{1cm}^{1\%}$ 32" should read --$E_{1cm}^{1\%}$ = --.

Column 4, line 36: "$C_{44}H_{7411}$" should read --$C_{44}H_{74}O_{11}$--.

Column 4, line 59: "$Cu_{++}$" should read --$Cu^{++}$--.

Column 12, line 54: "remian" should read --remain--.

Column 14, line 20: The phrase --Example 3-- should be inserted between lines 19 and 21.

Column 14, line 28: "filered" should read --filtered--.

Column 18, line 3: "given" should read --give--.

Column 21, line 36: "eacept" should read --except--.

Signed and Sealed this

Fifteenth Day of May 1979

[SEAL]

Attest:

RUTH C. MASON
Attesting Officer

DONALD W. BANNER
Commissioner of Patents and Trademarks